United States Patent
Wu et al.

(10) Patent No.: US 8,244,340 B2
(45) Date of Patent: Aug. 14, 2012

(54) METHOD, SYSTEM AND DEVICE FOR SLEEP STAGE DETERMINATION USING FRONTAL ELECTRODES

(75) Inventors: Jianping Wu, Mississauga (CA); Ronald Leon Kurtz, Oakville (CA); Aaron Phillip Weinroth, Thornhill (CA)

(73) Assignee: Natus Medical Incorporated, San Carlos, CA (US)

( * ) Notice: Subject to any disclaimer, the term of this patent is extended or adjusted under 35 U.S.C. 154(b) by 1450 days.

(21) Appl. No.: 11/615,584

(22) Filed: Dec. 22, 2006

(65) Prior Publication Data

US 2008/0154111 A1   Jun. 26, 2008

(51) Int. Cl.
*A61B 5/04* (2006.01)

(52) U.S. Cl. ........................................ 600/544; 600/545

(58) Field of Classification Search .......... 600/529–545, 600/382–383
See application file for complete search history.

(56) References Cited

U.S. PATENT DOCUMENTS

| | | | |
|---|---|---|---|
| 3,313,293 A | 4/1967 | Chesebrough et al. | |
| 3,669,119 A | 6/1972 | Symmes | |
| 3,675,649 A | 7/1972 | Basham et al. | |
| 4,928,696 A | 5/1990 | Henderson et al. | |
| 5,245,995 A | 9/1993 | Sullivan et al. | |
| 5,280,791 A | 1/1994 | Lavie | |
| 5,353,788 A * | 10/1994 | Miles | 128/204.23 |
| 5,398,682 A | 3/1995 | Lynn | |
| 5,479,934 A | 1/1996 | Imran | |
| 5,485,851 A | 1/1996 | Erickson | |
| 5,645,054 A | 7/1997 | Cotner et al. | |
| 5,662,101 A | 9/1997 | Ogden et al. | |
| 5,682,878 A | 11/1997 | Ogden | |
| 5,794,615 A | 8/1998 | Estes | |
| 5,803,065 A | 9/1998 | Zdrojkowski et al. | |
| 5,901,704 A | 5/1999 | Estes et al. | |
| 5,904,141 A | 5/1999 | Estes et al. | |
| 5,970,975 A | 10/1999 | Estes et al. | |
| 5,999,846 A | 12/1999 | Pardey et al. | |
| 6,032,065 A | 2/2000 | Brown | |
| 6,085,747 A | 7/2000 | Axe et al. | |
| 6,091,973 A | 7/2000 | Colla et al. | |
| 6,128,521 A | 10/2000 | Marro et al. | |
| 6,138,675 A | 10/2000 | Berthon-Jones | |
| 6,230,049 B1 | 5/2001 | Fischell et al. | |
| 6,240,921 B1 | 6/2001 | Brydon et al. | |
| 6,272,378 B1 | 8/2001 | Baumgart-Schmitt | |

(Continued)

OTHER PUBLICATIONS

Multi-Centre Comparison of Five Eye Movement Detection Algorithms. Journal of Sleep Research, 4, pp. 119-130, 1995.

(Continued)

*Primary Examiner* — Patricia Mallari
*Assistant Examiner* — Michael D'Angelo
(74) *Attorney, Agent, or Firm* — Temmerman Law Office; Mathew J. Temmerman

(57) ABSTRACT

The described embodiments relate generally to methods, systems and devices for sleep stage determination using frontal electrodes. Certain embodiments relate to a system for sleep stage determination comprising a sensing unit and a processing unit. The sensing unit is positioned over a forehead area of a patient and has first, second and third electrodes for positioning at locations on or adjacent the forehead area for detecting electrical potentials of a human head. The processing unit is coupled to the sensing unit for receiving biological signals corresponding to the detected electrical potentials and processing the biological signals to determine a sleep stage of the patient. The processing of the biological signals is based on a plurality of rules.

13 Claims, 8 Drawing Sheets

U.S. PATENT DOCUMENTS

| | | |
|---|---|---|
| 6,363,270 B1 | 3/2002 | Colla et al. |
| 6,397,845 B1 | 6/2002 | Burton |
| 6,427,689 B1 | 8/2002 | Estes et al. |
| 6,431,171 B1 | 8/2002 | Burton |
| 6,467,477 B1 | 10/2002 | Frank et al. |
| 6,539,940 B2 | 4/2003 | Zdrojkowski et al. |
| 6,564,797 B1 | 5/2003 | Mechlenburg et al. |
| 6,609,517 B1 | 8/2003 | Estes et al. |
| 6,629,527 B1 | 10/2003 | Estes et al. |
| 6,640,806 B2 | 11/2003 | Yurko |
| 6,654,626 B2 | 11/2003 | Devlin et al. |
| 6,826,426 B2 | 11/2004 | Lange et al. |
| 6,993,380 B1 | 1/2006 | Modarres |
| 2002/0029004 A1 | 3/2002 | Starr et al. |
| 2004/0204656 A1 | 10/2004 | Tolvanen-Laakso et al. |
| 2005/0043652 A1* | 2/2005 | Lovett et al. ............ 600/595 |
| 2005/0059898 A1 | 3/2005 | Gobel |
| 2005/0261559 A1 | 11/2005 | Mumford et al. |
| 2005/0268916 A1* | 12/2005 | Mumford et al. ......... 128/207.13 |
| 2006/0258930 A1 | 11/2006 | Wu et al. |

OTHER PUBLICATIONS

± 1.5g-3g Three Axis Low-g Micromachined Accelerometer. www.freescale.com, accessed May 2006.

Customised Printed Circuit Sensors & Electrodes. www.vermed.com/custom.php, accessed May 2006.

Chen et al., "A Comparison of Patient State Index and Bispectral Index Values During the Perioperative Period", Society for Technology in Anesthesia, 2002, pp. 1669-1674.

Gora et al., "Evidence of a Sleep-Specific Blunted Cortical Response . . . ", American Journal of Respiratory, and Critical Care Medicine, vol. 166, 2002, pp. 1225-1234.

* cited by examiner

METHOD, SYSTEM AND DEVICE FOR SLEEP STAGE DETERMINATION USING FRONTAL ELECTRODES

TECHNICAL FIELD

The described embodiments relate to a method, system and device for sleep stage determination using frontal electrodes. In particular, embodiments involve positioning of at least three electrodes on human forehead positions.

BACKGROUND

For medical diagnostic purposes, it can be useful to determine the sleep stages experienced by a person during sleep. Such sleep stage determination has traditionally been performed in a laboratory setting, in which the patient is asked to sleep while undergoing the testing. Under such conditions, the patient may to experience abnormal sleep patterns.

The sleep stage determination in such a laboratory setting is commonly performed by affixing a plurality of electrodes on the patient's scalp at various standard positions according to the 10-20 system of electrode placement. Some electrodes are positioned to sense electroencephalographic (EEG) signals, while other electrodes may be positioned to detect electromyographic (EMG) signals or electrooculographic (EOG) signals. The EEG, EMG and EOG signals may be provided to a processing system, including, for example, a neural network for use in determining the stage of sleep experienced by the person according to the detected signals.

The described embodiments attempt to address or ameliorate one or more of the disadvantages or shortcomings associated with existing sleep stage determination methods or systems, or to at least provide a useful alternative thereto.

SUMMARY

The described embodiments relate generally to methods, systems and devices for sleep stage determination using frontal electrodes. Certain embodiments relate to a system for sleep stage determination comprising a sensing unit and a processing unit. The sensing unit is positioned over a forehead area of a patient and has first, second and third electrodes for positioning at locations on or adjacent the forehead area for detecting electrical potentials of a human head. The processing unit is coupled to the sensing unit for receiving biological signals corresponding to the detected electrical potentials and processing the biological signals to determine a sleep stage of the patient. The processing of the biological signals is based on a plurality of rules.

The rules may be stored in a data store associated with the processing unit. The processing unit may store data associated with the biological signals internally or it may communicate with an external device.

The sensing unit may comprise a flexible member having the first, second and third electrodes located thereon. The first electrode may be located on the flexible member for positioning adjacent a nasion area of the head. The second and third electrodes may be located on the flexible member for positioning over opposed lateral forehead portions. One of the first, second and third electrodes may act as a reference electrode. Conductors may be formed on the flexible member for electrically coupling the first, second and third electrodes to an output connector coupled to the processing unit.

The sensing unit may comprise a fourth electrode located on the flexible member intermediate the second and third electrodes for positioning over a central forehead portion. The second and third electrodes may be located on the flexible member for positioning higher on the forehead than Fp1 and Fp2 electrode positions. The fourth electrode may be located on the flexible member for positioning above the first electrode. The first and fourth electrodes may be located on the flexible member for positioning along a vertical center line of the head. The fourth electrode may be located on the flexible member for positioning lower on the forehead than a Fz electrode position and may act as a reference electrode. The second and third electrodes may be located on the flexible member for positioning laterally beyond respective Fp1 and Fp2 electrode positions.

The second, third and fourth electrodes may be positioned along a line. The first, second and third electrodes may be positioned in a triangular configuration. The triangular configuration may be an isosceles triangular configuration. The first, second, third and fourth electrodes may be positioned in a T-shaped, cross-shaped or Y-shaped configuration. The conductors may comprise a printed flexible material. The second and third electrodes may have a separation of 70 to 110 mm, 80 to 100 mm, or about 90 mm. The first and fourth electrodes may have a separation of 35 to 55 mm, 40 to 50 mm, or about 44 mm.

The processing unit may comprise a signal conditioning unit for receiving the detected electrical potentials, conditioning the electrical potentials to generate the biological signals and providing the biological signals to a processor within the processing unit. The plurality of rules may be stored in the data store. The plurality of rules may represent physiological conditions correlated with particular biological signals. The output connector may be formed at an end of a connector limb of the flexible member.

The electrical potentials may correspond to at least one of EEG, EOG and EMG signals. A pre-processing unit may be comprised in the processing unit. The pre-processing unit may comprise a wireless transmitter for wirelessly transmitting the biological signals to a receiver of the processing unit. The wireless transmitter may be a low-power, short-range transmitter. The first, second and third electrodes may be removably attachable to the sensing unit. The flexible member may comprise a flexible plastic substrate or a woven material.

Other embodiments relate to a method of sleep stage determination, comprising receiving electrical potentials corresponding to biological signals from an electrode assembly positioned over a head of a patient; processing the biological signals to determine EEG signals, EOG signals and EMG signals; and determining a sleep stage of the patient based on the EEG signals, the EOG signals and the EMG signals and a plurality of rules.

The rules may be based on empirically derived correlations of EEG, EOG and EMG signal activity with one or more stages of sleep. The electrode assembly may comprise first, second and third electrodes positioned at locations on or adjacent the forehead area, the first electrode being positioned adjacent a nasion area of the head and the second and third electrodes being positioned over respective laterally opposed forehead areas. The second and third electrodes may be positioned above and laterally beyond respective Fp1 and Fp2 positions.

The method may further comprise, prior to the step of receiving, positioning a sensing unit comprising the frontal electrode assembly over the forehead area. The sensing unit may be configured to sense electrical potentials corresponding to the biological signals.

The sleep stage may be determined on an epoch by epoch basis. For an epoch, the step of determining may include evaluating the EEG signals, the EOG signals and the EMG signals received during the epoch according to the plurality of rules and assigning a sleep stage categorization to the epoch. The step of determining may include evaluating the EEG signals, the EOG signals and the EMG signals received during a plurality of epochs according to the plurality of rules and assigning a sleep stage categorization to the epoch. The step of determining may be based on previous undecided epochs and last determined epochs and the plurality of rules.

Other embodiments relate to computer readable storage storing computer program instructions, which, when executed by a computer processor, cause the computer process to perform the method of: receiving electrical potentials corresponding to biological signals from an electrode assembly positioned over a head of a patient; processing the biological signals to determine EEG signals, EOG signals and EMG signals; and determining a stage of sleep of the patient based on the EEG signals, the EOG signals and the EMG signals and a plurality of rules.

BRIEF DESCRIPTION OF THE DRAWINGS

Embodiments are described in further detail below by way of example only, with reference to the accompanying drawings, in which.

DETAILED DESCRIPTION

Figure 1:
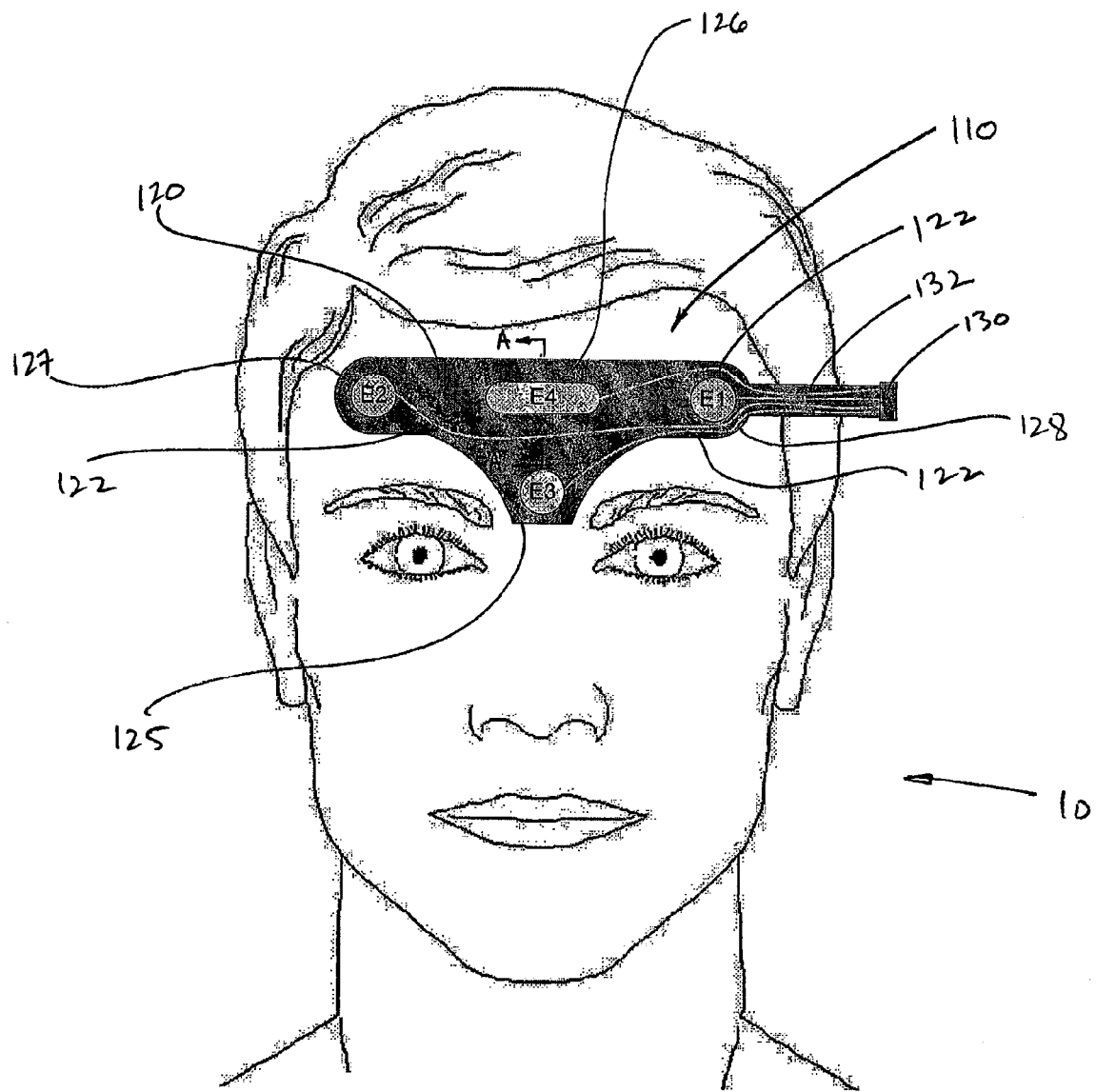
FIG. 1 is a front view of a sensing unit for use in sleep stage determination.

Referring to FIGS. 1 to 4, embodiments of a device comprising a sensing unit for use in sensing electrical potentials for sleep stage determination are shown and described. In the drawings and description, like reference numerals are used to indicate like features, functions and/or elements as between the drawings.

In this description, reference to terms implying a directional orientation, such as lateral, vertical, below, above or downward, are intended to be viewed as if the sensing unit is positioned on a forehead of a human head, while that head is upright. Accordingly, "vertical" is intended to denote directions from the top of the skull toward the neck, while "lateral" is intended to denote positions or directions to one side of a vertical midline of the head extending along the frontal line of symmetry of the face (i.e. perpendicular to vertical). For example, in this context, the eyes are laterally spaced relative to the vertical midline. Thus, "lateral" as applied to the forehead means extending across the forehead between the eyebrows and the hairline and, depending on the shape of the particular forehead, possibly extending around toward the upper temple area.

Terms used herein that imply direction or orientation, such as those mentioned above, are used for ease of description only and are not intended to be a limitation on the described embodiments when they are not in use on the forehead.

Referring in particular to FIG. 1, there is shown a sensing unit 110 positioned on the forehead of a human head 10. Sensing unit 110 has an electrode array including four electrodes E1, E2, E3 and E4 formed thereon for overlying exposed skin surfaces of the forehead and nasion areas. Electrodes E1, E2, E3 and E4 are used to detect electrical potentials corresponding to EEG, EMG and EOG signals during a sleep study.

Sensing unit 110 comprises a flexible plate-like member 120 formed roughly in a T-shape when viewed from the front while worn on the head 10. A lower portion 125 of flexible member 120 projects downwardly from the substantially laterally extending body of flexible member 120. Lower portion 125 houses electrode E3 so as to be positioned to at least partly overlie the nasion area or an area adjacent thereto. Depending on the forehead structure of the head 10, electrode E3 may be positioned slightly above the nasion area, but generally on a centre line extending vertically through the forehead intermediate the eyes and eyebrows.

Electrodes E1, E4 and E2 are spaced laterally across sensing unit 110. Electrode E4 acts as a ground electrode relative to the measured potentials from electrodes E1, E2 and E3. Electrodes E1 and E2 are positioned in laterally extending wings 127 and 128 located on respective right and left sides of the head 10 (as seen from the patient's perspective). Electrodes E1 and E2 and wings 128 and 127 are positioned widely (laterally) so that, for most forehead sizes and structures, the electrodes E1, E2 are respectively positioned on the forehead above and laterally beyond a vertical centerline through each eye. The greater lateral spacing of electrode E1 and E2 allows the sensing of a greater amount of relevant EEG data.

Ground electrode E4 is positioned generally centrally on sensing unit 110 within a central area 126 of flexible member 120.

As shown in FIG. 1, flexible member 120 has a connector limb 132 extending from a left side (seen from the patient's perspective) thereof and a connector 130 at an end of connector limb 132. Connector 130 is arranged to electrically couple conductors 122 extending through sensing unit 110 to a processing unit 520 (shown and described in relation to FIG. 5), thereby forming an electrical connection between the processing unit and the electrodes E1, E2, E3 and E4 to which conductors 122 are electrically coupled.

According to one embodiment, sensing unit 110 is formed mostly of flexible materials for placement on a forehead structure and for generally conforming to the shape of the forehead structure. Certain parts of sensing unit 110 (for example, those around the electrodes) have an adhesive substance, such as a foam adhesive layer, on an underside thereof, for affixing the sensing unit 110 to the forehead prior to conducting the sleep study. Flexible circuitry, comprising conductors 122, extends through sensing unit 110 from each of the electrodes E1, E2, E3 and E4 to connector 130. Thus, sensing unit 110 can be used with forehead structures of varying shapes and sizes due to its flexibility and ability to conform and adhere to such varying forehead structures, as required.

Figure 2:
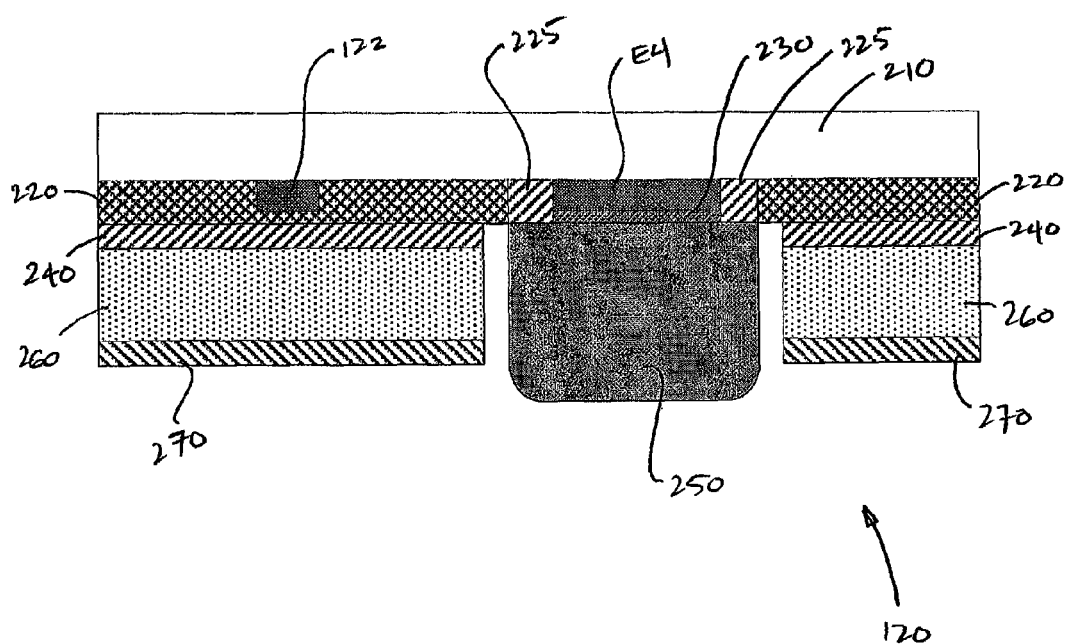
FIG. 2 is an illustrative side cross-section of the sensing unit of FIG. 1, taken along the line A-A.

Sensing unit 110 is shown in FIG. 2 in partial cross-section, taken along line A-A of FIG. 1. Flexible member 120 employs a substrate 210 of a flexible material such as a medical grade polyester film (or other material having similar properties). Substrate 210 forms the top (or upper or outer) layer facing away from the forehead. Substrate 210 has sufficient rigidity to form the base for flexible circuitry to be printed (or otherwise formed) thereon and enable subsequent conductive and insulating layers to be formed thereon, while having sufficient flexibility to enable the entire flexible member 120 to bend to generally conform to the shape of the forehead to which it is to be affixed.

The substrate 210 may be about 3 to 8 thousandths of an inch thick, for example. Adhesive 270 is of a relatively weak strength and is used to affix at least a part of the flexible member 120 to the skin of the forehead. Adhesive 270 is provided on a layer of medical grade adhesive foam 260 of approximately 1/32 of an inch thickness. The foam 260 is adhered to an insulation layer 220 on the substrate 210 on one side with a relatively strong adhesive 240 and has adhesive 270 on the opposite side for removable attachment to the test subject. Insulation layer 220 is applied directly to the substrate 210 to insulate electrical conductors and is formed of an appropriate epoxy or resin. The electrodes E1 to E4 may comprise a silver or silver chloride layer formed on the substrate 210. The substrate 210 has flexible circuit tracings formed thereon for constituting the conductors 122 between electrodes E1 to E4 and output connector 130. Such circuit tracings may comprise silver and preferably have a dielectric layer (such as insulation layer 220) formed thereover.

Prior to affixation to the forehead, sensing unit 110 may have backing sheets (not shown) on those parts of sensing unit 110 that have an adhesive substance 270 on their undersides for adhesion to the skin. Each such backing sheet is removed immediately prior to adhesion of the relevant part of sensing unit 110 to the corresponding forehead area or areas. For electrodes E1 to E4, an area of conductive gel (not shown), such as hydrogel, is interposed between the respective electrode and the skin surface (instead of the adhesive foam 260), for facilitating conductivity of electrical signals between the electrodes E1 to E4 and the skin.

Sensing unit 110 is a generally flat device, as viewed from the user's perspective, prior to affixation to the test subject. However, sensing unit 110 does have several layers, as described above. In use of sensing unit 110, and with the backing sheets removed, the adhesive foam 260 and electrodes E1 to E4 are positioned to lie against the skin. These skin contact surfaces may be conveniently referred to as being formed on the underside of the sensing unit 110. Printed labeling, including affixation instructions, may be provided on the side of sensing unit 110 that does not contact the skin.

Electrodes E1 to E4 are formed on substrate 210, either directly or on a thin priming or separation layer (not shown) coating the underside of substrate 210. Electrodes E1 to E4 are electrically coupled to output connector 130 via conductors 122 in the form of flexible circuit tracings formed on substrate 210. As with electrodes E1 to E4, conductors 122 may be directly formed on substrate 210 or may be separated therefrom by a priming or separation layer. Portions of flexible member 120 that are not to be exposed to the forehead (such as conductors 122) are covered by insulation layer 220.

In the embodiment shown in FIG. 2, electrode E4 comprises a silver chloride layer 230 on its outer face for facilitating conductivity with the skin via a conductive gel in contact with electrode E4. The conductive gel is provided as a liquid hydrogel and is impregnated into a porous foam sponge 250 that contacts the skin when the sensing unit 110 is positioned on the patient's forehead. Sponge 250 is adhered to substrate 210 by an adhesive layer 225 disposed around the electrodes. In order to allow for compression of the sponge during skin contact, a gap may be formed on either side of the sponge 250 between the sponge 250 and the foam layer 260.

In an alternative embodiment, a substantially more viscous conductive gel can be used instead of the sponge 250 and liquid hydrogel, in which case the adhesive layer 225 and the compression gap are not required. The above impregnated sponge arrangement and the viscous hydrogel arrangement are both commercially available from Vermed, Inc. of Bellows Falls, Vt., USA.

Adhesive layer 270 and conductive sponge 250 may be covered by the protective backing sheet or layer (not shown) so that the adhesive and conductive qualities of the adhesive layer 270 and conductive sponge 250 are preserved until application of flexible member 120 to the forehead. The total thickness of sensing unit 110, including substrate 210, may be in the range of 0.7 to 1.5 millimeters, approximately.

The embodiment shown in FIG. 2 is not to scale, is for purposes of illustration only and some variations or modifications may be made, depending on the specific requirements of the sensing unit embodiment and methods of forming it.

While the sensing unit embodiments shown and described herein generally have a unitary flexible member including two wings and a projecting portion, alternatively each of the areas or portions of the sensing unit having electrodes may be formed on a separate, but connected, substrate.

In an alternative embodiment of sensing unit 110, metallic disk electrodes may be used with a flexible member formed of molded plastic, such as a polyvinylchloride (PVC) plastic. In such an embodiment, the plastic is preferably relatively thin and flexible to accommodate the contours of the wearer's forehead, while having sufficient structural integrity and rigidity to maintain the electrodes in their respective positions. Such a molded plastic flexible member may be shaped similarly to flexible member 120 and may employ a suitable adhesive to secure it in place on the forehead. Alternatively, or in addition, a strap or other mechanical means may be used to secure the sensing unit 110 in place on the wearer's forehead.

Figure 3A:
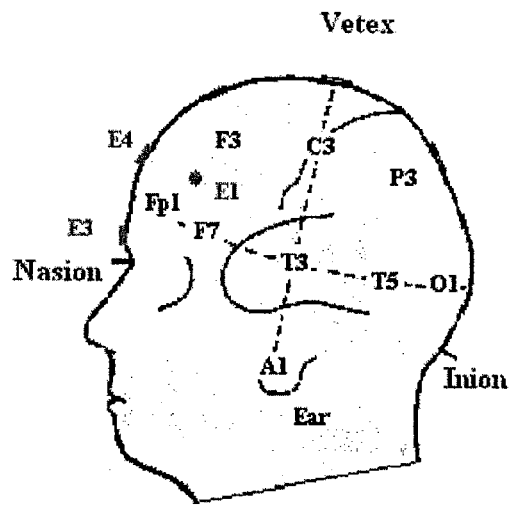
FIG. 3A is a representative side view of a human head, showing standard electrode positions and electrode positions according to described embodiments.
Figure 3B:
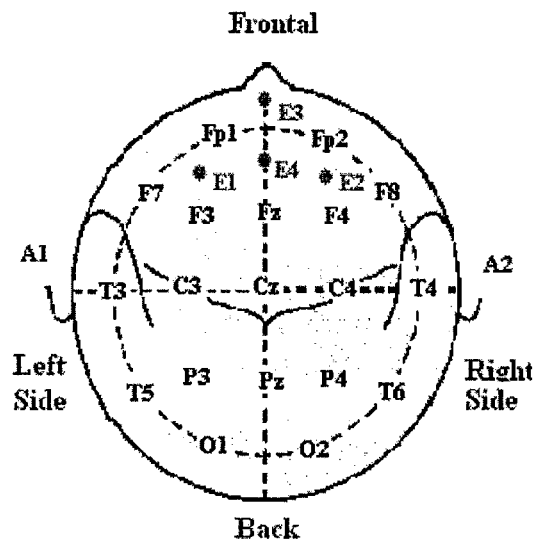
FIG. 3B is a representative plan view of a human head corresponding to FIG. 3A.
Figure 4:
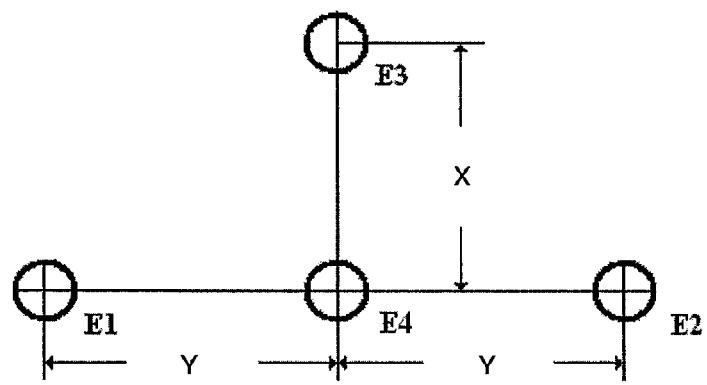
FIG. 4 is a schematic representation of the relative positions of electrodes on the sensing unit.

Referring in particular to FIGS. 3A, 3B and 4, the positioning of electrodes E1, E2, E3 and E4 is described in further detail. FIGS. 3A and 3B indicate the likely positions of electrodes E1 to E4 on a human head, relative to the standard 10-20 electrode positions. As can be seen from FIGS. 3A and 3B, reference electrode E3 is positioned adjacent the nasion area. Electrode E3 is located on flexible member 120 so that, for most forehead structures, it will be positioned immediately above the nasion and in between the eyebrows. Electrode E3 is thus positioned on the vertical centerline of the head in a position lower than the line extending laterally through frontal positions Fp1 and Fp2.

Electrode E4 is positioned on the midline (vertical centerline) below frontal position Fz but above the lateral frontal line extending through frontal positions Fp1 and Fp2. Electrodes E3 and E4 are separated by a distance X, as shown in FIG. 4, where X may be about 35 to 55 mm. In one embodiment, X may be about 40 to 50 mm. In a further embodiment, X may be about 44 mm.

As shown in FIG. 4, electrodes E1 to E4 are arranged in a T-shaped configuration, with reference electrode E3 at a bottom of the T and electrodes E1, E2 and E4 forming the top line of the T. In alternative embodiments, the electrode configuration need not be strictly T-shaped. For example, ground electrode E4 may be shifted up or down so that it is not strictly in line with electrodes E1 and E2.

Further, electrodes E1, E2 and E3 are arranged in a triangular configuration, where the distance between electrodes E1 and E3 is the same as the distance between electrodes E2 and E3, but is not the same as the distance between electrodes E1 and E2. Thus, electrodes E1, E2 and E3 are arranged in an isosceles triangular configuration. This configuration allows the electrodes to be arranged in sensing pairs E1-E3 and E2-E3 to sense EEG, EOG and EMG potentials, while sensing electrode pair E1-E2 is also arranged to sense EEG, and EOG potentials. The E1-E3 and E2-E3 electrode pair orientations may be configured to be substantially orthogonal to each other.

Electrodes E1 and E2 are each laterally separated from electrode E4 by a distance Y that may be the same as distance X or may be different therefrom. The total distance (2Y) between electrodes E1 and E2 is, according to one embodiment, between about 70 and 110 mm. In another embodiment, the separation of electrodes E1 and E2 is about 80 to 100 mm. In a further embodiment, the separation is about 90 mm.

Electrodes E1 and E2 are located on flexible member 120 so as to be positioned on the forehead at forehead locations above and laterally beyond standard frontal positions Fp1 and Fp2, respectively. This wider and higher spacing of electrodes E1 and E2 across the frontal area allows for a greater range and quality of EEG potentials to be detected than if the standard Fp1 and Fp2 positions were used. This greater range can be used to compensate for the lack of a reference electrode positioned at A1 or A2 behind the ear.

The specific configuration of electrodes E1, E2 and E3 allows for simultaneous sensing of EEG, EOG and EMG potentials using a single electrode assembly on a flexible member that is easily applied by a patient to his or her own forehead prior to self-initiation of the sleep study. Thus, sensing device 110 is easily applied in a home setting without the need for the patient to be studied in an artificial environment and without the need for a medical technician to affix the electrodes to the patient's head 10.

In alternative embodiments of sensing unit 110, one or more of electrodes E1 to E4 may comprise a needle electrode specifically configured for EMG potential detection. Alternatively, or in addition, one or more of electrodes E1 to E4 may have a wireless transmitter associated therewith (instead of a conductor 122) for transmitting wireless signals to a nearby receiver, such as is described in U.S. patent application Ser. No. 11/130,221, entitled "Wireless Physiological Monitoring System", filed May 17, 2005, the entire contents of which is hereby incorporated by reference.

Although not shown in FIG. 1, embodiments of sensing unit 110 may have a strap attachable to each lateral wing 127, 128 for securing sensing unit 110 to head 10. Such a strap may be in addition or alternative to adhesive 270 for securing sensing unit 110 in place. In place of a strap, other means for securing the sensing unit to the head may be employed.

In a further embodiment, electrodes E1 to E4 are removably attachable to flexible member 120. In this embodiment, electrodes E1 to E4 are formed as metallic disk electrodes that have male snap connector parts on a back surface thereof for engaging a corresponding female snap connector part positioned on flexible member 120. In this embodiment, conductors 122 are electrically coupled to the female snap connector parts, which form a mechanical and electrical connection with the electrodes via the male snap connector parts on each electrode.

In this embodiment, the underside of flexible member 120 may not employ an adhesive to affix the flexible member 120 to the forehead. Rather, a strap or band may be used to secure the flexible member 120 in the appropriate location. In order to affix the electrodes E1 to E4 to the appropriate locations on the forehead and nasion areas, each electrode may be provided with a portion of adhesive foam around the outside of the conductive contact surface of the electrode. Alternatively, the conductive gel on the contact surface of the electrodes may have sufficient adhesive properties to obviate the use of adhesive foam portions around the electrodes.

The removably attachable electrode embodiment allows the flexible member 120 to be reusable while the electrodes can be disposed of after each use. In this embodiment, the flexible member 120 may be comprised of a material having greater flexibility and/or deformation properties than the polyester film or PVC described above. A suitable material may comprise a cloth or other woven material. Alternatively, the flexible member 120 may be comprised of a relatively more rigid material, such as PVC, although this rigidity is not strictly required if each electrode is held in place on the skin by the portion of adhesive material surrounding it.

While sensing unit 110 is described as being intended for use in sleep stage determination, the sensing unit 110 may also be used in connection with other apparatus or software to record other results of diagnostic significance. One example of such other apparatus is a mask for providing positive airway pressure (PAP) to the patient, such as is described in U.S. patent application Ser. No. 11/131,284, the entire contents of which is hereby incorporated by reference. Embodiments may also be used within the context of an intensive care unit (ICU), for example to assist in detection of a seizure, stroke, ischemia, burst-suppression or brain hemorrhage or for use in determining a level of consciousness, sedation or delirium of a patient.

According to alternative embodiments, additional sensors, which may be electrodes or other forms of sensors, may be provided for positioning at other locations on the head. For example, an additional electrode may be placed behind or in front of the ear or ears, for use as an active or reference electrode. Such additional sensors may be coupled (for example, on a unitary substrate) to flexible member 120 for electrical connection to the processing unit via connector 130. Alternatively, a separate connector and/or substrate may be used for electrically coupling the additional sensor or sensors to the processing unit.

While certain embodiments described herein contemplate the use of four electrodes E1 to E4 located on the flexible member 120, for each of those four electrodes, more than one electrode may be used in place of the single electrode. In still further embodiments, the sensing unit 110 may employ more than four electrodes at various positions on the flexible member 120. In a further alternative embodiment, the ground electrode E4 may be omitted or its position varied.

While the configuration of the electrode array of sensing unit 110 is shown arranged in a T-shaped configuration, alternative configurations, for example where the central ground electrode E4 is positioned higher or lower, may be employed. However, electrode configurations that necessitate placement of one of the electrodes over a hair-covered part of the scalp or forehead are less desirable than those that allow placement of the electrodes over hairless areas of the scalp or forehead. Thus, shapes analogous to a T-shape, such as a cross-shape, Y-shape or other shapes having laterally extending wings and a downwardly projecting portion, may be employed to a similar effect to the embodiments using a T-shaped electrode configuration on the flexible member. In one embodiment, the lateral wings of the flexible member 120 may extend further laterally and droop down, in a shape similar to ram's horns, to cover the temple areas on either side of the head. This allows additional electrodes to be placed over the temple areas for increased EEG sensing capability.

Referring now to FIGS. 5 to 9, embodiments of a system and method for use in processing measured electrical potentials corresponding to biological signals for sleep stage determination are shown and described. These embodiments employ the embodiments of sensing unit 110 described above.

Figure 5:
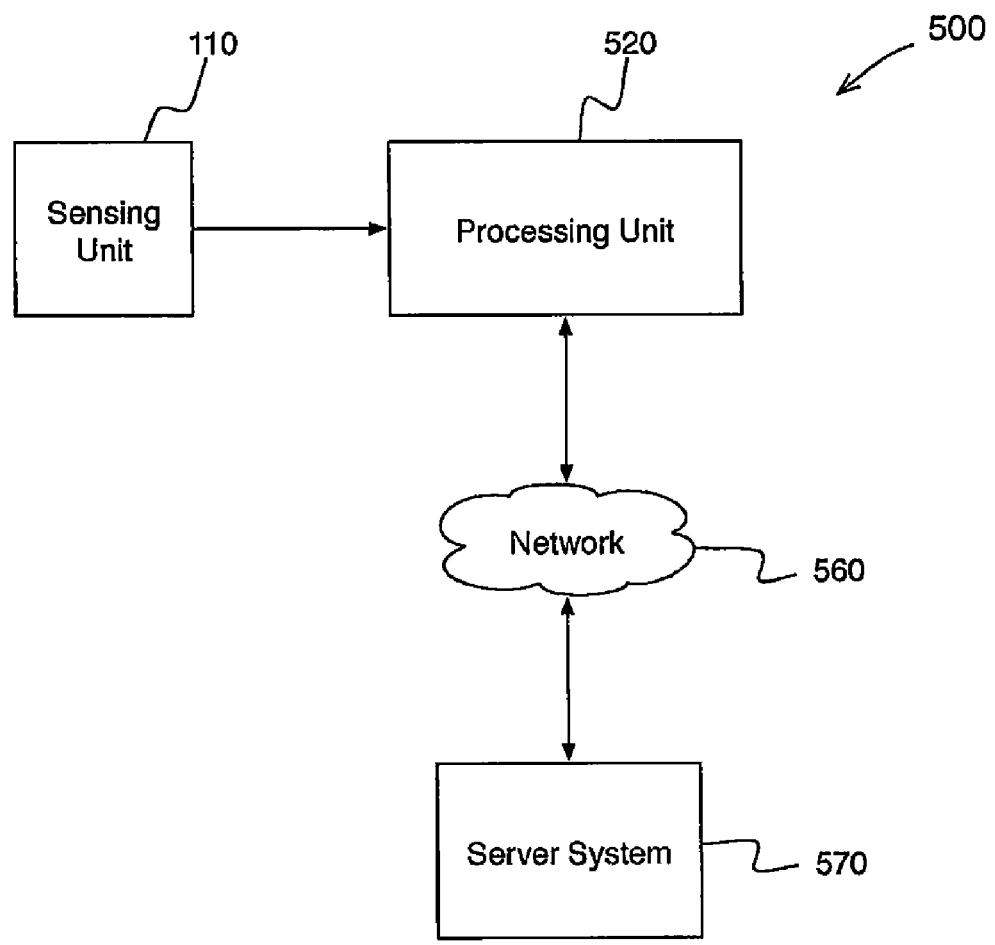
FIG. 5 is a block diagram of a system for sleep stage determination.

Referring in particular to FIG. 5, there is shown a system 500 for sleep stage determination including the sensing unit 110 and a processing unit 520 in communication with, and coupled to, sensing unit 110. Processing unit 520 accepts electrical potentials from sensing unit 110 as input, transforms the received electrical potentials into suitable biological signal data and performs digital signal processing on the biological signal data. Processing unit 520 may also accept instructions via a user interface 660 (FIG. 6) or provide feedback related to operation of system 500. Processing unit 520 may further communicate over a network 560 with a server system 570 in order to, for example, exchange data or instructions. An example embodiment of processing unit 520 is shown in more detail in FIG. 6.

Network 560 may comprise a suitable computer or telephone network, such as a local area network (LAN). Other networks, such as a wireless local area network (WLAN), the public Internet, or a public switched telephone network (PSTN), may also form part of network 560.

Server system 570 may be used to provide various facilities better suited to a centralized system, such as: storage of patient records; storage of sleep data; management of remote processing units; downloading updated software to procession unit 520; facilities for communicating other data, such as user instructions or administrative commands, to remote devices; and facilities for receiving data, such as user queries or diagnostic information, from remote devices. In one embodiment, server system 570 may be comprised of a plurality of physical computers, not necessarily co-located.

Figure 6:
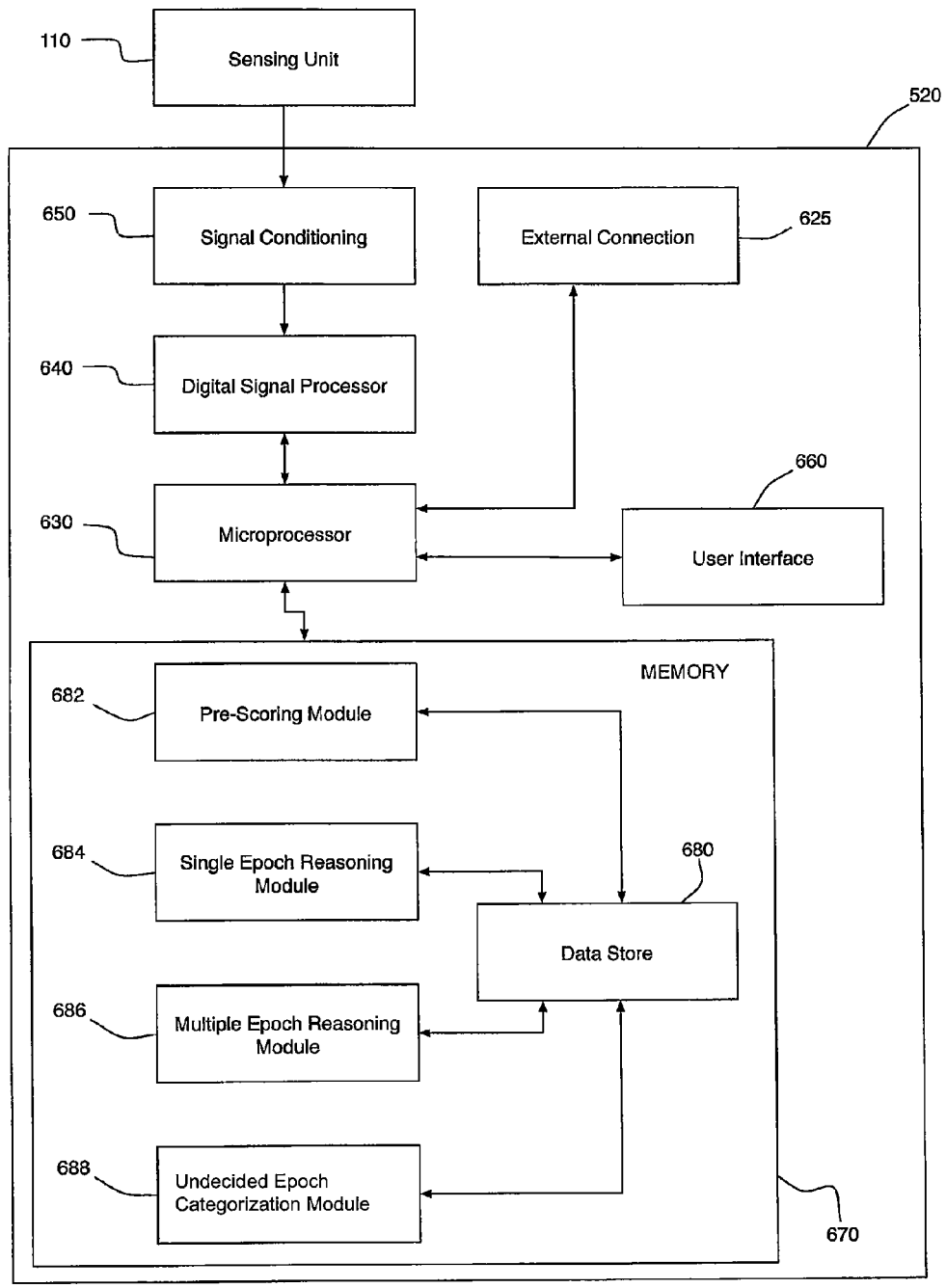
FIG. 6 is a more detailed block diagram of portions of a system for sleep stage determination corresponding to FIG. 5.

Referring in particular to FIG. 6, processing unit 520 is shown in further detail. Processing unit 520 contains elements required for processing the electrical potentials captured by sensing unit 110. Electrical potentials are received from sensing unit 110 and undergo signal conditioning using a signal conditioning module 650 to transform the received electrical potentials into suitable biological signal data. Such signal conditioning may include filtering signals in the received data into various frequency bands, as well as amplification and removal of any DC offset.

Conditioned signals are supplied to a digital signal processor 640 for analysis under the control of, or in combination with, a microprocessor 630. Processed biological signal data is stored in a memory 670 by microprocessor 630. Microprocessor 630 retrieves stored data from memory 670 as needed, for example to provide output or perform further processing. Microprocessor 630 also transmits data to user interface 660, for example, to generate a display to a user of processing unit 520. Additionally, microprocessor 630 may receive operational instructions from a user via user interface 660.

Signal conditioning module 650 may comprise electronic circuitry on an application-specific integrated circuit (ASIC) designed for specific signal conditioning purposes, including amplification, removal of any DC offset, analog to digital signal conversion and filtering signals into various frequency bands. Alternatively, commercially available discrete components may be used to perform each function. Alternatively, a suitable combination of custom and commercial components may be used to perform the signal conditioning.

Digital signal processor (DSP) 640 may be a suitable commercially-available DSP, general purpose microprocessor, application specific integrated circuit (ASIC), field programmable gate array (FPGA), or a multiple or combination of any of these devices and is used to perform various calculations that require vector processing of data, such as Fast Fourier Transform (FFT) operations. In an alternative embodiment, a single module may perform the signal conditioning and DSP functions.

Microprocessor 630 may be a suitable commercially-available DSP, general purpose microprocessor, ASIC, FPGA, or a multiple or combination of any of these devices and is used to perform all computation and control functions not performed by other elements of the system, such as conditional branch evaluation, data input/output and device control.

User interface 660 consists of one or more input or output devices for human interaction, such as a keyboard, touchpad, printer or visual display. User interface 660 also comprises the output elements required to communicate data and command options to a user, such as forms, tables, buttons and other appropriate elements. User interface 660 may be adapted to accommodate a variety of uses or patients, for example to provide auditory or Braille output.

Microprocessor 630 may also communicate bi-directionally with an external connection 625. External connection 625 may comprise a wireless communication interface or a wired communication interface for communication with a remote device or system over, for example, network 560. Alternatively, external connection 625 may employ a standard communications interface, such as a Universal Serial Bus (USB), to communicate with an auxiliary or peripheral device to enable added functionality. Additionally, external connection 625 may also connect directly to another processing unit 520 or server system 570.

Microprocessor 630 reads, writes and otherwise manipulates data in memory 670. The contents of memory 670 may contain both biological signal data and operational instructions associated with a computer program to be used in evaluating the signal data. Memory 670 may be composed of both volatile and non-volatile memory components, including solid state, magnetic or optical storage, such as flash programmable memory and hard disk drives, or a combination thereof. In addition, future memory technologies may be employed as they become available and where they provide equivalent or enhanced functionality.

Several computer program modules are stored concurrently in memory 670, including: a pre-scoring module 682 for quickly categorizing easily-identified sleep stages; a single epoch reasoning module 684 for identifying sleep stages capable of being recognized within a single observation interval; a multiple epoch reasoning module 686 for identifying sleep stages which require signal observation over a multiplicity of observation intervals; and an undecided epoch categorization module 688 for categorizing previously uncategorized epochs. Each module may exist both as computer program instructions and as a computational representation of its current processing state.

Each of modules 682, 684, 686 and 688 is contained within memory 670 and may access and update the data store 680 as required, to update signal data and contextual information, receive updated signal data and contextual information, or otherwise read or manipulate relevant data. Contextual information includes sleep stage information as well as information regarding changes in the parameters used to determine a sleep stage. Contextual information may be combined with signal data to categorize an epoch as belonging to a particular sleep stage. For example, if the current epoch follows sleep stage1, AND the Beta1 power increases more than 50%, AND the spindle activity is not high, then the current epoch is scored (categorized) as Wake.

The functions of modules 682, 684, 686 and 688 may be further subdivided or supplemented with additional modules, for example to increase processing capacity. Additional detail regarding the function of modules 682, 684, 686 and 688 is provided below, particularly in paragraphs describing FIGS. 8 and 9 and in pseudo-code describing software operation.

One or more of the above elements, including signal conditioning module 650, digital signal processor 640, microprocessor 630, memory 670 and external connection 625, may be combined into a single physical device, for example, a field programmable gate array (FPGA).

Figure 7:
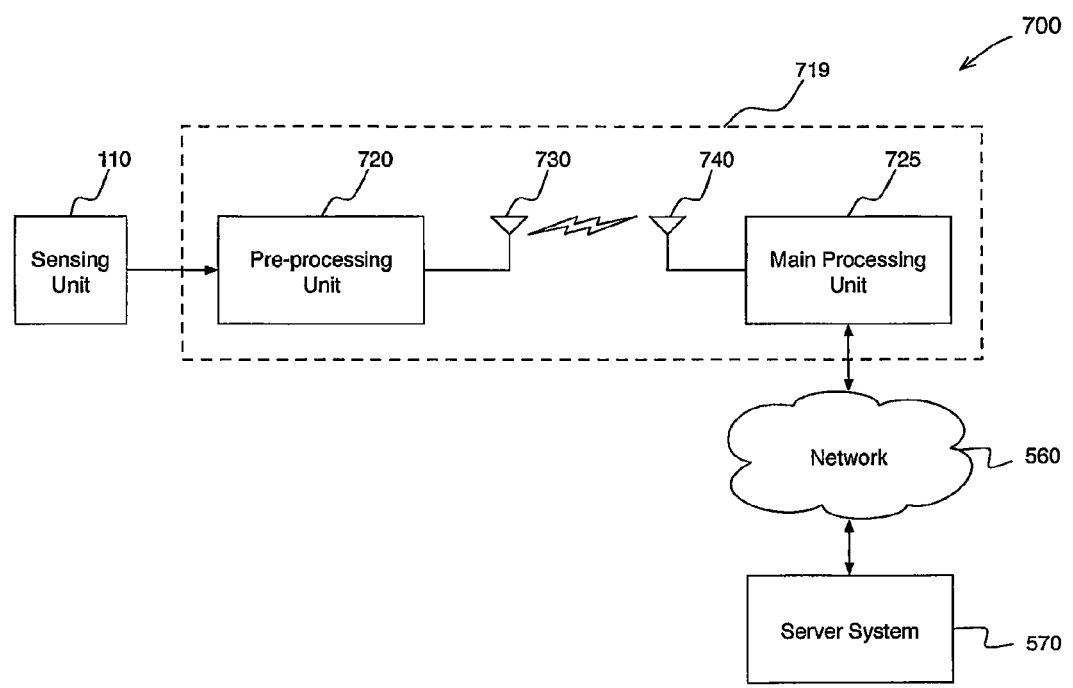
FIG. 7 is a block diagram of an alternative configuration of a system for sleep stage determination.

In an alternative embodiment, processing unit 520 may be subdivided into component units, for example, a pre-processing unit and a main processing unit, such as is shown in FIG. 7. Such an arrangement would allow for one main processing unit to service one or more pre-processing units, which may be helpful in certain clinical settings.

Referring in particular to FIG. 7, there is shown a system 700, comprising: sensing unit 110; a distributed processing unit 719 comprising a pre-processing unit 720, wireless communication interfaces (including transceivers) 730 and 740 and a main processing unit 725; network 560; and server system 570. Distributed processing unit 719 is functionally equivalent to processing unit 520, but possesses certain features, such as wireless operation and a many-to-one relationship of pre-processing units to main processing unit, that may make it more suitable for particular applications.

In this embodiment, sensing unit 110 is coupled (via connector 130) to pre-processing unit 720, which performs a subset of the functions, for example, signal conditioning and digital signal processing, performed by processing unit 520. In this embodiment, sensing unit 110, pre-processing unit 720 and wireless interface 730 effectively form a sub-system that can be worn by the patient without needing to be physically connected to, or co-located with, the main processing unit 725.

Pre-processing unit 720 uses wireless communication interface 730, which may employ a low-power, short-range antenna and a suitable wireless communication protocol, to communicate with wireless communication interface 740. Wireless communication interface 740 is connected to main processing unit 725, which performs the remainder of the functions of processing unit 520 not performed by pre-processing unit 720. One main processing unit 725 may communicate with a plurality of pre-processing units 720.

Main processing unit 725 may further communicate over network 560 with server system 570. In another alternative embodiment, both pre-processing unit 720 and main processing unit 725 may communicate directly with each other and/or with server system 570 over network 560.

Wireless communication interfaces 730 and 740 employ standard commercially-available hardware and operate over portions of the electromagnetic spectrum using common networking standards, for example the IEEE 802.11, Bluetooth or IrDA family of protocols. In an alternative embodiment, wireless communication interfaces 730 and 740 may be of a custom design to enhance certain characteristics, such as low power or secure operation, to suit the particular application of system 700. Future networking protocols and interfaces, possibly operating in other areas of the electromagnetic spectrum, may be substituted as they become available, where suitable.

In an alternative embodiment, for example, in a clinical or hospital environment, wireless operation may not be desirable or necessary. Therefore, wired communication interfaces, such as members of the IEEE 802.3 or 1394 families, may be used in place of wireless communication interfaces 730 and 740.

Collection of electrical potentials corresponding to biological signal data by sensing unit 110 occurs continuously over a period of a number of hours. At predetermined intervals, called epochs, an evaluation process is invoked to evaluate or categorize collected data. In an alternative embodiment, epoch frequency may be varied, for example, to increase the rate of data collection during periods of high activity.

Figure 8:
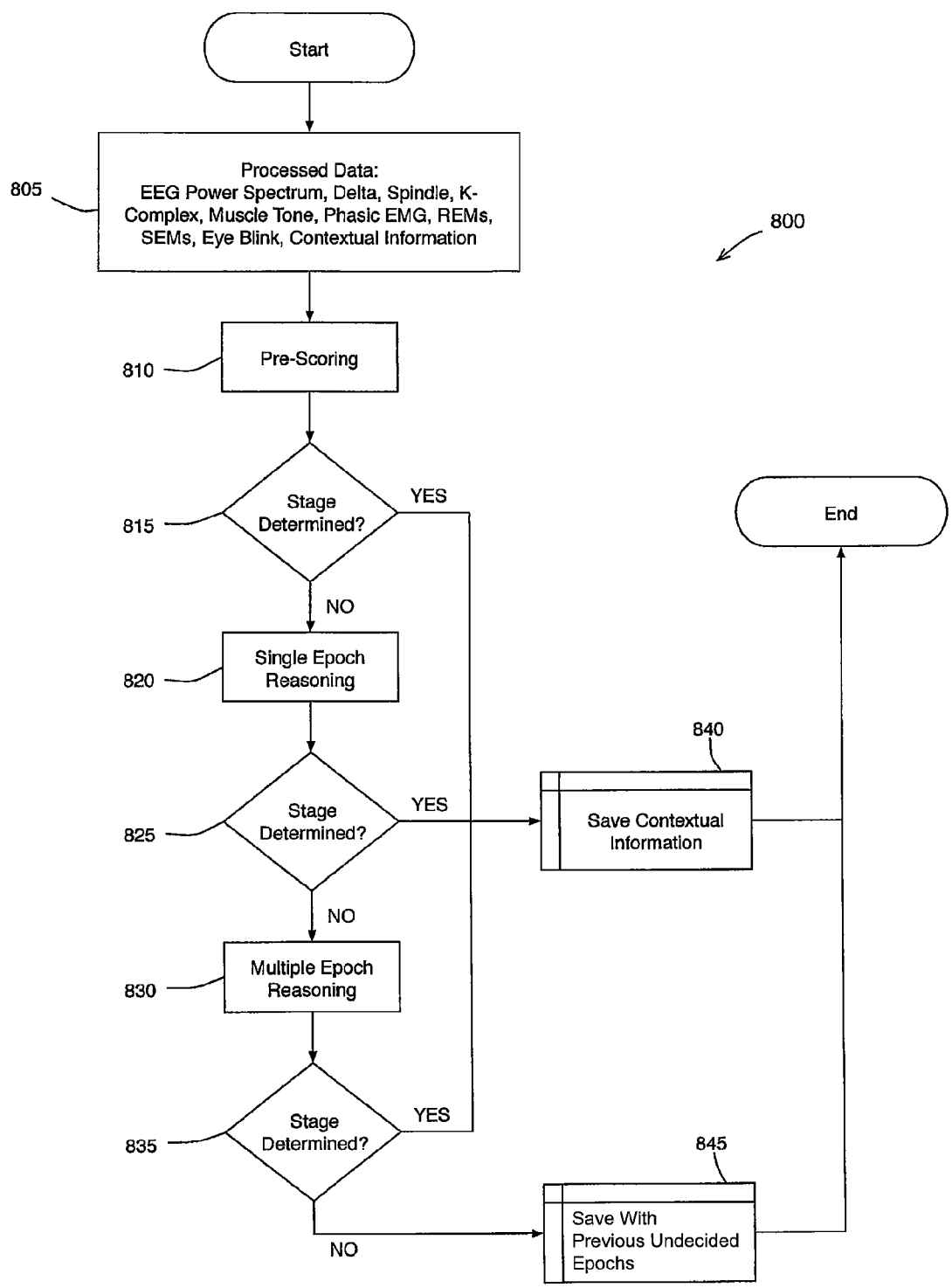
FIG. 8 is a flow chart of a method of sleep stage evaluation according to some embodiments.

Referring in particular to FIG. 8, there is shown a flow chart illustrating an evaluation process 800, which is an embodiment of one iteration of the process invoked for an epoch by processing unit 520 or main processing unit 725 to categorize collected signal data as belonging to a particular stage of sleep. Processed data, for example, consisting of EEG power spectrum, delta, spindle, K-complex waves, muscle tone, phasic EMG, rapid eye movements (REMs), slow eye movements (SEMs), eye blinks and other contextual information, is gathered at step 805 for pre-scoring evaluation at step 810.

Upon completion of pre-scoring step 810, a test is performed at step 815 to check if the sleep stage has been determined, based on the pre-scoring. If the sleep stage is determined, contextual information is saved at step 840 and process 800 ends. If the sleep stage cannot yet be determined, the evaluation process continues to single epoch reasoning, at step 820.

Upon completion of step 820, a test is performed at step 825 to check if the sleep stage has been determined, based on the single epoch reasoning. If the sleep stage is determined, contextual information is saved at step 840 and process 800 ends. If the sleep stage cannot yet be determined, the evaluation process continues to multiple epoch reasoning, at step 830.

Upon completion of step 830, a test is performed at step 835 to check if the sleep stage has been determined, based on the multiple epoch reasoning. If the sleep stage is determined, contextual information is saved at step 840 and process 800 ends. If the sleep stage cannot yet be determined, the data is saved as an undecided epoch, at step 845, and process 800 ends. An undecided epoch is equivalent to an unscored epoch or undetermined epoch.

Processed data gathered at step 805 is the collection of data obtained by sensing unit 110 and further conditioned and categorized by one or more of signal conditioning module 650, digital signal processor 640 and microprocessor 630. Processed data gathered at step 805 is stored in memory 670 in a format suitable for further evaluation.

Pre-scoring step 810, which is performed by microprocessor 630 executing pre-scoring module 682, evaluates processed data 805 to identify patterns that are easily categorized, for example, such as certain characteristics consistent with a waking stage. Upon evaluation of various pre-scoring rules, such as those described below in pseudo-code, it is determined at step 815 whether the sleep stage can be categorized by the pre-scoring process. If the pre-scoring step was successful at determining the sleep stage, the determined sleep stage is assigned to the epoch under consideration, contextual information is saved at step 840 and the current iteration ends. If no sleep stage has been determined, the process continues to single epoch reasoning at step 820.

Pseudo-code describing the decision process of one embodiment of pre-scoring step 810 is shown below. A glossary of acronyms and abbreviations used in the pseudo-code is provided in Table 3 below.

Pre-Scoring

```
IF (AftM || AftW)
    IF (Noisy || MA > 12 || FEMs >= 6 || (AlpPk && BSIHi))              Cstage = W
    ELSE IF (AlpEEG && (ASI >1.2 || FEMs >= 3 || BSI Decrs < 70%))
        OR (BtaEEG && (ASI > 0.6 || FEMs >= 3 || Tht Pwr Low))
        IF (FstWv Pwr VH && BSIHst && (FSPLow || AlpPwrHi || BSI
            Incrs > 20%))                                               Cstage = W
ELSE IF (FEMs >= 6 && BSIHi && ASI >= 0.6 && FSPLow)                    Cstage = W
ELSE IF (MA > 15)                                                       Cstage = MT
IF (Cstage == MT or Cstage == W)
    IF (AftR_W or AftR_M)                                               Cstage = W
    ELSE IF (AftR && Cstage == MT)                                      Cstage = R_T
ELSE IF (AftR && Cstage == W)                                           Cstage = R_W
ELSE        CONTINUE
```

Single epoch reasoning step 820, which is performed by microprocessor 630 executing single epoch reasoning module 684, evaluates processed data 805 to identify patterns that are capable of being categorized using information obtained only from the epoch that is currently being analyzed, for example such as REM sleep or transitions between REM sleep and another sleep stage. Upon evaluation of various single epoch reasoning rules such as those described below in pseudo-code, a decision is made at step 825. If the single epoch reasoning step is successful at determining the sleep stage, the determined sleep stage is assigned to the epoch under consideration, contextual information is saved at step 840 and the current iteration ends. If no sleep stage has been determined, the process continues to multiple epoch reasoning at step 830.

Pseudo-code describing the decision process of one embodiment of single epoch reasoning step 820 is shown below. A glossary of acronyms and abbreviations used in the pseudo-code is provided in Table 3 below.

Single Epoch Reasoning

```
IF (!AftW && !REMBgrd && !Wakening && !AftR && !BSIHst && Delta > 20%)
    IF (AftDS || DelPwr VH)                                              Cstage = SD
    ELSE                                                                 Cstage = S2
ELSE IF (!AftW && !AftDS && MslTLow && MA < 3 && Spindle not
        high && ATI < 0.4)
    IF (FstWv Pwr Low && FSPLwst && BSIHst)
        IF (BSI Incrs > 20% || AftS2)                                    Cstage = REM
        ELSE IF (AlpPwrLow && REMs > 0 && BSIHi && Spindle not
            found)
            IF (AftR && BSI Decrs < 50% && FSP Incrs < 200%)             Cstage = REM
            ELSE IF (!AftR && (BSILow || FSPHst))
                IF (AftS2 || S2Wvs)                                      Cstage = S2
                ELSE                                                     Cstage = S1
            ELSE IF (S2Wvs)                                              Cstage = R_S2
            ELSE                                                         Cstage = R_S1
ELSE IF (REMBgrd)
    IF (!S2Wvs && MA < 6 && AftR)                                        Cstage = REM
    ELSE IF (S2Wvs)                                                      Cstage = R_S2
    ELSE IF (MslTVH || AlpPk)                                            Cstage = R_M
    ELSE                                                                 Cstage = R_S1
ELSE IF ((AftR ||AftRLike) && MA < 6 && Spindle not high &&
        AlpPwrLow && !BSILow)
    IF (AlpPk || MslTVH)
        IF (AftR)                                                        Cstage = R_M
        ELSE IF (AftR_M or AftR_W)                                       Cstage = W
    ELSE IF (! AlpPk && HBSI > 6 && LFSP > 6)
        IF (!MslTLow && EEGPwr VH && REMs = 0)                           Cstage = R_M
        ELSE IF (BSIHst || (MslTLow && REMs > 0) || (MslTLow &&
                FSPLwst))                                                Cstage = REM
        ELSE IF (S2Wvs)                                                  Cstage = R_S2
        ELSE IF (AftR && (AlpPwrHi || FstWv Pwr High))                   Cstage = R_W
        ELSE                                                             Cstage = R_S1
ELSE IF (!S2Wvs && MA < 1 && (AftR || AftRLike) && ATILow &&
        EEGPwr Low && FstWv Pwr Low)
    IF (BSIHi && BSI Decrs < 50% && (FSPLow || FSP Incrs < 200%))        Cstage = R_S1
IF (Cstage == UNSCORED)     CONTINUE
ELSE                        STOP
```

Multiple epoch reasoning step 830, which is performed by microprocessor 630 executing multiple epoch reasoning module 686, evaluates processed data 805 to identify patterns that may require data from multiple epochs to categorize sleep stage, for example sleep stages S1 or S2. Upon evaluation of various multiple epoch reasoning rules such as those described below in pseudo-code, a decision is made at step 835. If the multiple epoch reasoning step is successful at determining the sleep stage, the determined sleep stage is assigned to the epoch under consideration, contextual information is saved at step 840 and the current iteration ends. If no sleep stage has been determined, the current epoch is categorized as undecided, data associated with the undecided epoch is saved at step 845 and the current iteration ends.

Pseudo-code describing the decision process of one embodiment of multiple epoch reasoning step 830 is shown below. A glossary of acronyms and abbreviations used in the pseudo-code is provided in Table 3 below.

Multiple Epoch Reasoning

```
IF (AlpPk && !SpnPk && Spindle not found && BSIHst)
    IF (! AlpPwrLow && ( AlpPwr or FstWv Pwr Incrs > 20%) )     Cstage = W
    ELSE                                                         Cstage = S1
ELSE IF ((AftW || AftM) && AlpPwrLow && AlpPwr Decrs > 40% &&
    FEMs < 3)
    IF (S2Wvs)                                                   Cstage = S2
    ELSE                                                         Cstage = S1
ELSE IF (!AftW && !MslTLow && BSIHst || FstWv Pwr VH &&
    (EEGPwr || FstWv Pwr VH) && !FSPHst)
    IF (AftS1 or AftR && Bta1Pwr Incrs > 50%)
        IF (Spindle not high)                                    Cstage = W
        ELSE IF (AlpPwr Incrs > 50%)
            IF (MslTVH)                                          Cstage = MT
            ELSE                                                 Cstage = W
        ELSE                                                     Cstage = S1
    ELSE IF (AftS2 || AftDS && Bta2Pwr Incrs > 100% && BSI VH)
        IF (FstWv Pwr High && Spindle not high)
            IF (MA > 2 || FSPHi)                                 Cstage = MT
            ELSE                                                 Cstage = W
        ELSE IF (Spindle not high && S2Wvs)                      Cstage = S2
        ELSE                                                     Cstage = S1
    ELSE IF (BSI VH && FSPLwst)
        IF (FstWv Pwr High && AftW or AftM)                      Cstage = W
        ELSE IF (EEGPwr VH)                                      Cstage = MT
        ELSE IF (AlpPwrLow)                                      Cstage = S1
    ELSE IF (BSIHi && REMs >= 4)
        IF (Spindle not high && FstWv Pwr High)                  Cstage = W
        ELSE IF (S2Wvs)                                          Cstage = S2
        ELSE                                                     Cstage = S1
ELSE IF (MA >= 3)
    IF ((BSIHi && FSPLow) || FstWv Pwr VH || (AftW || AftM))     Cstage = W
    ELSE IF (S2Wvs && !BSIHst)                                   Cstage = S2
    ELSE IF (FSPHst)                                             Cstage = S2
    ELSE                                                         Cstage = S1
ELSE IF (AftS2 || AftDS)
    IF (MslTVH && AlpPwr Incrs > 200% && BSIHi)                  Cstage = W
    ELSIF (AftDS && EEGPwr Incrs > 50% && Delta Incrs > 10%)     Cstage = S3
    ELSE IF (!BSIHi && S2Wvs)                                    Cstage = S2
    ELSE                                                         Cstage = S1
ELSE IF (AftS1 && FstWv Pwr High && AlpPwr Incrs > 20% &&
    FstWv Pwr Incrs > 20% && BSIHi)                              Cstage = W
ELSE                                                             Cstage = S1
```

Figure 9:
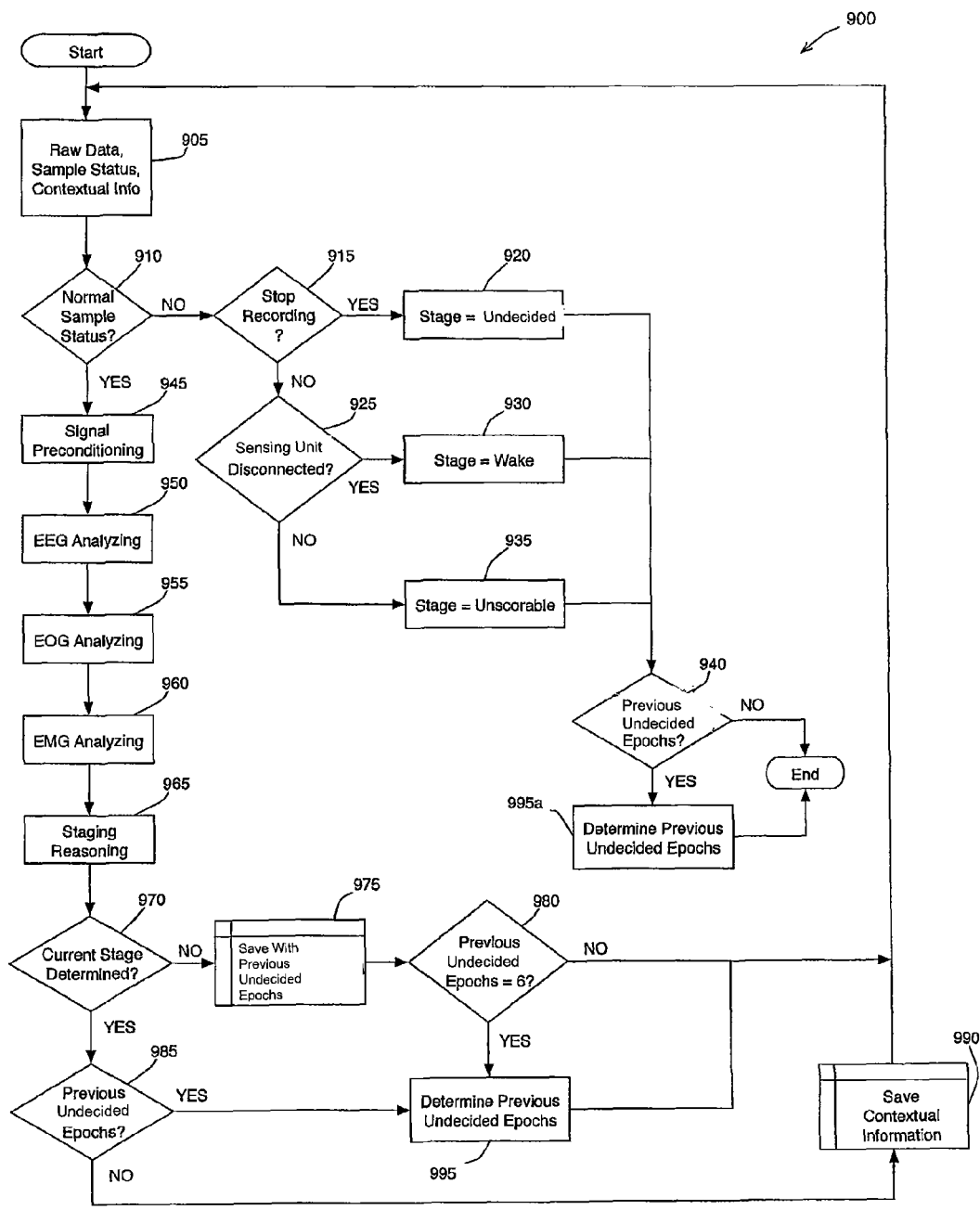
FIG. 9 is a flow chart of a method of sleep stage determination according to some embodiments.

Referring in particular to FIG. 9, there is shown a flow chart illustrating a process 900 describing operation of one embodiment of a sleep stage determination system, such as system 500 or 700. For each observational interval or epoch, which may be at a predetermined frequency or at a variable frequency influenced by prior epochs, raw data, sample status and contextual information is collected at step 905.

Collected data for the current sample is evaluated at step 910 to determine if it can be categorized as abnormal. Unless the sample is abnormal, the process continues to a full evaluation branch, beginning at step 945. The sample may be considered to be abnormal if it contains no signal data or only background noise, for example. This may indicate a fault in the sensing unit 110 or processing unit 520 or may be due to a disconnection of the sensing unit 110 from processing unit 520.

In the event that the current sample is identified as abnormal at step 910, a set of branch logic rules is evaluated, to diagnose system state and identify sleep stage, if possible. The diagnostic process begins at step 915 by first determining whether the system has been instructed to stop recording data, for example, if a patient or other person has issued a command through user interface 660. If so, the current sleep stage is marked as undecided at step 920. If the system has not been instructed to stop recording, a test is performed by processing unit 520 at step 925 to identify whether connecting sensing unit 110 has been disconnected from processing unit 520. This may occur intentionally, for example when the patient gets out of bed and leaves the room.

When the sensing unit 110 is disconnected from the processing unit 520, the input conductors of the processing unit 520 may pick up low level background noise. The processing unit 520 is configured to compare the received low level background noise to a noise level threshold and/or filtering circuit to determine whether the received noise is consistent with a disconnection. Alternatively, the processing unit 520 may comprise a circuit to sense when the connector 130 is connected or disconnected from the corresponding connecting part on or associated with processing unit 520. If the sensing unit 110 is determined by processing unit 520 to be disconnected, the current sleep stage is categorized as wake at step 930. Otherwise it is marked as unscorable at step 935

Upon completion of diagnostic tests, a further test is performed to identify if there exist previous undecided epochs at step 940. If there are none, the current iteration of process 900 ends. If there exist previous undecided epochs, an evaluation process is invoked at step 995*a* to determine previous undecided epochs, before process 900 is ended.

If the sample status is normal at step 910, signal preconditioning is performed at step 945 prior to EEG, EOG and EMG analysis at steps 950, 955 and 960, respectively. Step 945 is performed by signal conditioning module 650, whereas digital signal processor 640 and microprocessor 630 perform steps 950, 955 and 960. After signal analysis at steps 945 through 960, staging reasoning is conducted at step 965 using a process such as that described above with respect to FIG. 8. Upon completion of staging reasoning step 965, a set of rules is evaluated, beginning at step 970, to either complete the current iteration of process 900 or invoke an evaluation module to determine previous undecided epochs.

For each of steps 950, 955 and 960, the respective EEG, EOG and EMG signal analysis is performed in order to determine various characteristics and/or events or parameters indicated by the signals. This analysis may include suitable digital signal processing, including, for example, filtering, sampling Fourier transforms, or threshold comparisons. Such analysis may be carried out in the time domain or frequency domain, as appropriate. For example, the analysis may include analysis of the power spectral density in the frequency domain. Steps 950, 955 and 960 may be performed in the sequence indicated or the order of these steps may be changed or they may be performed simultaneously.

In the signal preconditioning step 945, the biological signal data is digitized and amplified, if necessary, by signal conditioning unit 650. Further, digital signal processor 640 processes the biological signal data to obtain the EEG, EMG and EOG signal data (as described further below), after which the EEG, EMG and EOG signal data are analyzed (as described further below) to provide the processed data referred to above in relation to step 805.

If the current sleep stage is determined at step 970 and there are no previous undecided epochs found at step 985, microprocessor 630 saves contextual information at step 990, for example, to data store 680, and ends the current iteration. If the current sleep stage is determined at step 970 and there are extant previous undecided epochs at step 985, an evaluation process is invoked to determine previous undecided epochs at step 995; upon completion of which the current iteration ends.

If the current sleep stage is not determined at step 970, the process will save the current epoch with previous undecided epochs at step 975, for example, to data store 680. If there exist 6 previous undecided epochs at step 980 an evaluation process is invoked to determine previous undecided epochs at step 995; upon completion of which the current iteration ends. If there are fewer than 6 previous undecided epochs at step 980, the current iteration ends immediately. Using 6 as the upper limit of previous undecided epochs assumes epochs of 30 seconds and that the 3 minute smoothing rule applies, whereby if a K complex or spindle is not seen within 3 minutes of the previous K complex or spindle, the sleep stage defaults to stage one sleep (S1). A predetermined number other than 6 may be used in step 980 according to alternative configurations, for example where shorter or longer epochs are used.

The evaluation process to determine previous undecided epochs at step 995, which is performed by undecided epoch categorization module 688, evaluates prior undecided epochs and last detected epochs, not necessarily in sequential order, to identify patterns that could not otherwise be identified.

Pseudo-code describing the decision process of one embodiment of a determination of previous undecided epochs, such as that at steps 995 and 995*a*, is shown below. A glossary of acronyms and abbreviations used in the pseudo-code is provided in Table 3 below.

Determine Previous Undecided Epochs

```
IF (Only one epoch && PUE == R__W,
R__S1, R__S2 or R__M)
    IF (PUE == R__W)                          Cstage = W
    ELSE IF (PUE == R__S1)                    Cstage = S1
    ELSE IF (PUE == R__S2)                    Cstage = S2
    ELSE IF (PUE == R__M)                     Cstage = MT
ELSE IF (NDE == W)
    LOOP the Previous Undecided Epochs List
        IF (PUE == REM__S1)                   Cstage = S1
        ELSE IF (PUE == R__S2)                Cstage = S2
        ELSE IF (PUE == R__M)                 Cstage = MT
        ELSE                                  Cstage = W
ELSE IF (NDE == REM)
    LOOP the Previous Undecided Epochs List
        IF (PUE == R__W, R__M, W or MT)
            IF (LDE == W or MT)               Cstage = W
            ELSE                              Cstage = MT
        ELSE                                  Cstage = REM
ELSE IF (NDE == MT)
    LOOP the Previous Undecided Epochs List
        IF (PUE == R__S1)                     Cstage = S1
        ELSE IF (PUE == R__S2)                Cstage = S2
        ELSE                                  Cstage = W
ELSE
    LOOP the Previous Undecided Epochs List
        IF (LDE == S2)                        Cstage = S2
        ELSE IF (LDE == REM)                  Cstage = REM
        ELSE IF (PUE == R__W or R__M)         Cstage = MT
        ELSE IF (PUE == R__S1)                Cstage = S1
        ELSE IF (PUE == R__S2)                Cstage = S2
        ELSE                                  Cstage = NDE
```

Upon completion of the determination of previous undecided epochs at steps 995 and 995*a*, contextual information for the relevant epochs is saved in a data store, such as data store 680.

Processing and analysis of the biological signal data to obtain the EEG, EMG and EOG data may be performed as described below. The EEG signals are derived from channels associated with electrode pairs E1-E3 and E2-E3. The EEG signals are obtained by filtering the biological signal data with a band pass filter to obtain frequencies between 0.5 and 30 Hz.

Each epoch of 30 seconds is divided into 10 equal segments and each 3-second data segment is subject to a Fast Fourier Transform (FFT) to obtain the power spectral density for each EEG sub activity. Table 1 below shows the frequency bands for a number of recognized EEG sub activities.

TABLE 1

| Frequency ranges of EEG sub activities | | | | | |
|---|---|---|---|---|---|
| Frequency | Alpha | Beta1 | Beta2 | Delta | Sigma | Theta |
| Low | 7.5 | 16.0 | 20.0 | 1.0 | 12.0 | 3.0 |
| High | 9.5 | 20.0 | 28.0 | 2.5 | 15.0 | 7.0 |

Thus, for example, for each 3 second data segment, digital signal processor 640 calculates the power of the EEG signals in the Alpha band between 7.5 and 9.5 Hz, and so on for each of the other EEG sub activities. In addition to the power spectral analysis of each 3-second data segment, several parameters are calculated by DSP 640, including a Beta/Sigma index (BSI), an Alpha/Theta index (ATI) and the frontal spindle (FSP). The BSI is the ratio between the power of the Beta2 band and that of the Sigma band. The ATI is the ratio between the power of the Alpha band and that of the Theta band. The FSP is the calculated spectral power of the sigma band.

Further features are extracted from the EEG signal data that involve determination of the total duration for which the signal data is within a certain amplitude range for each epoch. Specifically, Delta, Spindle and K-complex activities are extracted from the EEG signals, based on the frequency and amplitude parameters listed in Table 2 below.

TABLE 2

Parameters for detection of delta, spindle, K-complex

| Parameters | Delta | Spindle | K-complex |
|---|---|---|---|
| Filter frequency (Hz) | 0.5-3.5 | 9.0-15.0 | 3.0-7.0 |
| Amplitude range (μV) | 35-150 | 15-60 | 30-70 |

The parameters listed in Table 2 are used to calculate the proportion of the epoch for which the EEG signal data is within the amplitude range indicated for the listed delta, spindle and K-complex frequencies. For example, if greater than 50% of the epoch has signals in the amplitude range of 35 to 150 μV for delta frequencies between 0.5 and 3.5 Hz, then this information may be used to determine that the epoch should be decided as belonging to deep sleep stage S4. If greater than 20% of the epoch is within the amplitude range for the delta frequencies, then the epoch may be decided as belonging to deep sleep stage S3. Deep sleep stages S3 and S4 may be collectively scored as "deep sleep" if the amplitude range for the delta frequencies exceeds a minimum threshold. Such a minimum threshold is configurable, but may be between 2% and 20%, for example.

The EMG analysis of the biological signal data is performed based on the signals received from channel E1-E2 and band-pass filtered between 20 and 40 Hz. The EMG analysis involves calculation of tonic and phasic activities of muscles in the forehead and vicinity. Tonic activity is associated with a relaxed, restful state and is referred to also as muscle tone or tonus. Tonic activity is used to detect changes in muscle tone for REM and NREM sleep. Phasic activity is associated with sudden increases in muscle activity and is used for the detection of movement arousal.

To avoid EMG bursts that may be associated with the phasic activity, which can be a result of a muscle twitch or movement, obscuring the tonic activity, the tonic activity is calculated using the inter-quartile range method, instead of integrating the rectified EMG data of the whole epoch. The inter-quartile range is calculated as the difference between the 75th percentile of sample amplitudes (often called Q3) and the 25th percentile (called Q1). The inter-quartile range is also sometimes called the H-spread. Period analysis is used to detect peaks in the EMG signal data and the amplitudes of the detected peaks are sorted and the muscle tone is then calculated as the difference between Q3 and Q1. The calculated EMG tonus is used as a threshold to detect EMG burst phasic activities.

EMG burst detection is performed in a similar manner to the EEG feature extraction described above, but with a frequency range of 10 to 40 Hz. If any EMG bursts are detected in an epoch, the 3-second data segments including the detected EMG bursts are eliminated from consideration and the rest of the data segments in the epoch are used to again calculate the EMG tonus. Additionally, DSP 640 determines the average amplitude of the EMG tonus, as this may be relevant to determination of which sleep stage the epoch should be assigned to. For example, if the average amplitude of the EMG tonus is low, then this indicates a REM sleep stage.

For the EOG analysis, left and right EOG signal data are extracted from the biological signal data via channels E1-E3 and E2-E3 band-pass filtered between 0.5 and 30 Hz. The EOG signal data are analyzed by DSP 640 for eye activities, including eye blink, rapid eye movement and slow eye movement. The EOG signal data is analyzed with respect to an amplitude threshold, frequency range (peak to peak intervals), rising slope and falling slope of the EOG signal wave form to detect eye movements. Wave forms in the EOG signal data corresponding to eye movements are detected separately between the left and right EOG channels. Only those eye movements that are negatively correlated from left and right EOG channels are considered as true.

Some high amplitude (up to several hundred micro volts), low frequency (0.1 to 1.0 Hz) waveforms may be detected in frontal channels. The waveforms may be, for example, EEG delta waves, eye movement activities, or signal noise generated by body movements or other sources. With limited information available from the frontal channels, it may be difficult to identify the source of such waveforms, which in turn may result in difficulties in determining the sleep stage. For example, false detection of eye movements or delta activities may be caused by noise associated with body movements. As a result, it may be difficult to distinguish Wake from stage 1, stage 2 from deep sleep, REM from stage 1, and Wake from deep sleep when alpha intrusion occurs in deep sleep.

In one embodiment, one or more body movement sensors may be used for transmitting signals to processing unit 520 or pre-processing unit 720 over a body movement channel. Information or signals received over the body movement channel can be helpful for sleep staging with frontal channels by assisting to identify the source of the high amplitude slow waveforms (HASWs). For example, when body movement is detected (with the body movement channel), the HASWs can be considered to be noise and the epoch can be scored as either Wake or MT (movement time). Further, if the epoch immediately follows or precedes a Wake stage, or if there is dominant alpha activity found in the current epoch, then the epoch can be scored as Wake. Otherwise, the epoch is scored as MT.

When no body movement is detected, the HASWs can be regarded as eye movements or delta activities and the stage of the epoch can therefore be narrowed down to Wake, REM or S1 if the background activities are dominated by fast activities (alpha, beta activities); or the epoch is scored as S2 or delta sleep if the dominant activities are slow waveforms (delta activities). The exact stage is determined by other information, for example such as contextual information, EEG power spectra, and percentage of duration of detected delta activities over the epoch.

The one or more body movement sensors for providing signal data over the body movement channel are positioned on, or relative to, a part of the body away from the head. Such sensors may sense movement by use of one or more accelerometers affixed to the body or they may sense movement by detection of EMG signals derived from an EMG sensor, for example. Alternatively, the body movement sensors may be located away from the body and may employ or promote movement detection techniques, such as are known in the art, including, but not limited to, optical imaging. An example of a suitable accelerometer for use in the one or more body movement sensors is an accelerometer made by FreeScale Semiconductor, Inc. of Austin, Tex. under the MMA7260Q product series.

The body movement sensors may be coupled to processing unit 520 or pre-processing unit 720 directly or via sensing unit 110. Communication of the signal data obtained by the body movement sensors to processing unit 520 or pre-processing unit 720 may be by way of a wired or wireless connection. If an EMG signal detection component is used in the one or more body movement sensors, it may be coupled with a wireless transmitter, as described in U.S. patent application Ser. No. 11/130,221.

Provision of the described means for detecting body movement enables the identification of HASWs in each epoch being considered, which in turn assists in determining the correct sleep stage of the subject.

While the above description provides examples of embodiments, it will be appreciated that some features and/or functions of the described embodiments are susceptible to modification and change without departing from the spirit and principles of operation of the described embodiments. Accordingly, what has been described is intended to be illustrative of the invention and the described embodiments, rather than being a limiting and/or exclusive definition.

TABLE 3

| Glossary of terms, acronyms and abbreviations | |
|---|---|
| Acronym or Abbreviation | Description and Definition |
| AftDS | The immediate previous epoch is scored as Deep Sleep (S3 or S4) |
| AftM | The immediate previous epoch is scored as MT |
| AftR | The immediate previous epoch is scored as REM |
| AftRLike | The immediate previous epoch is scored as R_M, R_W, R_S1 or R_S2 |
| AftR_M | An epoch which is scored as Movement Time for which the immediate previous epoch is scored as REM |
| AftR_W | An epoch which is scored as Wake for which the immediate previous epoch is scored as REM |
| AftS1 | The immediate previous epoch is scored as S1 |
| AftS2 | The immediate previous epoch is scored as S2 |
| AftW | The immediate previous epoch is scored as Wake |
| Alp | EEG alpha sub band: 7.5~9.5 Hz |
| AlpEEG | Alpha type EEG: Peak found in the alpha sub band in Wake epochs. |
| AlpPk | Peak found in the alpha sub band on EEG power spectra |
| AlpPwr | EEG power of spectra of alpha sub band |
| AlpPwrLow | AlpPwr is low when it is < the average AlpPwr of previous S1 epochs |
| AlpPwrHi | AlpPwr is high when it is: >2 times of the average AlpPwr of previous S1, OR > Average AlpPwr of wake epochs without eye movements |
| ASI | Ratio of Alpha and Spindle band EEG power spectra |
| ATI | Alpha Theta Index: Ratio of Alpha and Theta band EEG power spectra |
| ATILow | Alpha Theta Index Low: when the ratio of alpha and theta sub bands power of spectra is <0.4. |
| Bta1 | EEG beta1 sub band: 16~20 Hz |
| Bta1Pwr | EEG power of spectra of Bta1 sub band |
| Bta2 | EEG beta2 sub band: 20~28 Hz |
| BtaEEG | Beta type EEG: Peak found in the beta sub band in Wake epochs. |
| Bta2Pwr | EEG power of spectra of Bta2 sub band |
| BtaPk | Peak found in the Bta1 sub band on EEG power spectra |
| BSI | Ratio of Bta2 and Spindle band EEG power spectra |

TABLE 3-continued

| Glossary of terms, acronyms and abbreviations | |
|---|---|
| Acronym or Abbreviation | Description and Definition |
| BSIHi | Current BSI level is high if it is not BSIHst, AND: >50% of its average over previous S1, REM and Wake epochs, OR >2 times its average over previous S2 epochs; >1.5 |
| BSIHst | Current BSI level is highest if it is: > its average over previous S1, REM epochs or 80% of wake epoch average, OR >2.0 AND >50% of its average over previous S1 epochs, OR >3.0 |
| BSILow | Current BSI level is low if it is not BSIHst, not BSIHi, not BSILwst, AND: < its average over previous SD epochs, OR <1.2 times its average over previous S2 epochs, OR <0.5 |
| BSILwst | Current BSI level is lowest if it is not BSIHst, not BSIHi, AND: << Of its average over previous S2 epochs, OR <20% of its average over previous REM epochs, OR <0.1 |
| BSI VH | BSI very High if: BSIHst or BSIHi and BSI increased more than 50%. |
| Cstage | Stage of current epoch (being analyzed) |
| Decrs | Decreased compared to last epoch (e.g. Alpha Incrs >0.2 = alpha decreased more than 20% than last epoch) |
| Del | EEG delta sub band: 1~2.5 Hz |
| DelPwr VH | EEG power of spectra of delta sub band is very high, when it is: $>5 \times 10^7$, $\mu V^2$ AND >2 times its value in previous S2, AND ATI <0.4. |
| Delta | Duration of detected delta waves (in seconds). |
| EEGPwr | EEG power of spectra of the sub band ranging from 1~28 Hz. |
| EEGPwr Low | EEGPwr is low when it is: <10% of the average of previous wake epochs with eye movements; OR <20% of the average of wakes epochs without eye movements. |
| EEGPwr VH | EEGPwr very high when it is: > the average of previous wake epochs with eye movements; OR >3 times the average of previous wake epochs without eye movements. |
| FSP | Frontal spindle: 10.5~14 Hz |
| FSPHi | Current FSPPwr level is high if it is not FSPLwst, not FSPLow and not FSPHst. |
| FSPHst | Current FSPPwr level is low if it is not FSPLwst and not FSPLow, AND: > its average over previous SD epochs, OR >80% of its average over previous S2 epochs, OR >3 times its average over previous S1 epochs, OR >4 times its average over previous wake epochs. |

TABLE 3-continued

Glossary of terms, acronyms and abbreviations

| Acronym or Abbreviation | Description and Definition |
|---|---|
| FSPLow | Current FSPPwr level is low if it is not FSPLwst, AND: < its average over previous S1 epochs, OR <1.2 times its average over previous REM epochs, OR <50% of its average over previous S2 epochs. |
| FSPLwst | Current FSPPwr level is lowest if it is: < its average over previous REM, wake epochs, or 80% of S1 epochs; OR <30% of its average over previous S2 epochs. |
| FSPPwr | Value of EEG power spectra of frontal spindle (ranging from 10.5~14 Hz) |
| FstWv | EEG power spectra of fast waves (ranging from 8 to 30 Hz). |
| FstWv Pwr High | FstWv Pwr is high when it is: > its average over previous S1 epochs, AND >7.5 × $10^6$ $\mu V^2$. |
| FstWv Pwr Low | FstWv is low when it is < its average value of previous S1 epochs. |
| FstWv Pwr VH | FstWv is very high when it is > its average value of previous Wake epochs. |
| FEMs | Number of Fast Eye Movements: REMs + eye blinks; |
| HBSI | The number of segments (out of total 10 for each epoch) for which BSI is BSIHi. Each 30 second epoch is divided evenly into ten 3 second segments. The EEG power spectra of each is analyzed independently and categorized. |
| Incrs | Increased compared to last epoch (e.g. Alpha Incrs >0.2 = alpha increased more than 20% than last epoch) |
| LDE | Last determined epoch: the epoch for which a sleep stage was determined and which is immediately BEFORE current previous undecided epoch. |
| LFSP | The number of segments (out of total 10 for each epoch) for which FSP is FSPLow |
| MA | Duration of detected movement arousal (in seconds) |
| MslTLow | Muscle tone level is Low, if it is: < its average over previous S1, S2 and SD epochs; OR <1.2 times its average over previous REM epochs. |
| MslTVH | Muscle tone level is very high, if it is: >2 times its average value of previous S1, S2, SD and REM epochs. |
| MT | Movement Time sleep stage |
| NDE | Next determined epoch: the epoch for which a sleep stage was determined and which is immediately AFTER current previous undecided epoch. |
| Noisy | The signals are noisy: more than 50% of the epoch in which signal amplitude is higher than 200 μV for EEG, 500 μV for EMG and 300 μV for EOGs. |
| PUE | Previous undecided epochs |
| REM | Sleep stage REM |
| REMBgrd | REM background activities when: MslTLow, AND AftR, AND REMs >0, AND !BSILwst, AND !AlpPk, AND !FstWv Pwr VH, AND FSPLow |
| REMs | Number of detected rapid eye movement(s) |
| R_M | REM or MT |
| R_S1 | REM or S1 |
| R_S2 | REM or S2 |
| R_W | REM or Wake |
| S1 | Sleep stage 1 |
| S2 | Sleep stage 2 |
| SD | Delta (deep) sleep stage (S3 or S4) |
| S2Wvs | Spindle, K-Complex found in the epoch |
| Spindle not high | Frontal spindle activities are not high when: the duration of detected spindles <10% of the epoch length AND FSPLow |
| SpnPk | Peak found in the FSP sub band on EEG power spectra |
| Tht | EEG theta sub band: 3~7 Hz |
| Tht Pwr Low | Theta sub band power of EEG spectra is low when it is: <2.0 times its lowest value. |
| W | Sleep stage Wake |
| Wakening | Wakening activities: when MslTVH, BSIHi or BSIHst, and AlpPwr increased more than 200%. |
| && | Logic AND |
| \|\| | Logic OR |
| ! | Logic NOT |

The invention claimed is:

1. A method of sleep stage determination, comprising:
receiving electrical potentials corresponding to biological signals from an electrode assembly positioned over a head of a patient;
processing the biological signals to determine EEG signals, EOG signals and EMG signals;
calculating, with a processor, a pre-score based on the EEG signals, the EOG signals and the EMG signals and a plurality of rules;
using said processor for determining based on said plurality of rules and said pre-score whether the sleep stage can be categorized by the pre-score;
checking whether a sleep stage has been categorized based on said pre-score using said processor; and
when said checking step determines that the sleep stage could not be categorized based on said pre-score, determining the sleep stage based on at least one epoch.

2. The method of claim 1, wherein the rules are based on empirically derived correlations of EEG, EOG and EMG signal activity with one or more stages of sleep.

3. The method of claim 1, wherein the electrode assembly comprises first, second and third electrodes positioned at locations on or adjacent the forehead area, the first electrode being positioned adjacent a nasion area of the head and the second and third electrodes being positioned over respective laterally opposed forehead areas.

4. The method of claim 3, wherein the second and third electrodes are positioned above and laterally beyond respective Fp1 and Fp2 positions.

5. The method of claim 1, further comprising, prior to the step of receiving, positioning a sensing unit comprising the frontal electrode assembly over the forehead area, the sensing unit being configured to sense electrical potentials corresponding to the biological signals.

6. The method of claim 1, wherein in said determining the sleep stage based on at least one epoch step, the sleep stage is determined on an epoch by epoch basis.

7. The method of claim 6, wherein for an epoch, the step of determining includes evaluating the EEG signals, the EOG signals and the EMG signals received during the epoch according to the plurality of rules and assigning a sleep stage categorization to the epoch.

8. The method of claim 7, wherein the step of determining includes evaluating the EEG signals, the EOG signals and the EMG signals received during a plurality of epochs according to the plurality of rules and assigning a sleep stage categorization to the epoch.

9. The method of claim 7, wherein the step of determining is based on previous undecided epochs and last determined epochs and the plurality of rules.

10. The method of claim 1, further comprising receiving further electrical potentials corresponding to body movement of the patient, wherein the determining is also based on the further electrical potentials.

11. The method of claim 10, further comprising positioning one or more body movement sensors in relation to a body of the patient away from the head to provide the further electrical potentials.

12. The method of claim 11, wherein the one or more sensors comprise one or more accelerometers.

13. The method of claim 11, wherein the one or more sensors comprise one or more electromyographic sensors.

* * * * *